(12) United States Patent
Saiki

(10) Patent No.: US 8,512,638 B2
(45) Date of Patent: Aug. 20, 2013

(54) MICROCHIP AND ANALYZER USING THE SAME

(75) Inventor: Hiroshi Saiki, Ehime (JP)

(73) Assignee: Panasonic Corporation, Osaka (JP)

( * ) Notice: Subject to any disclaimer, the term of this patent is extended or adjusted under 35 U.S.C. 154(b) by 460 days.

(21) Appl. No.: 12/447,564

(22) PCT Filed: Oct. 23, 2007

(86) PCT No.: PCT/JP2007/070603
§ 371 (c)(1),
(2), (4) Date: Apr. 28, 2009

(87) PCT Pub. No.: WO2008/053743
PCT Pub. Date: May 8, 2008

(65) Prior Publication Data
US 2010/0074801 A1 Mar. 25, 2010

(30) Foreign Application Priority Data
Oct. 31, 2006 (JP) .................................. 2006-295159

(51) Int. Cl.
*B01L 3/00* (2006.01)
(52) U.S. Cl.
USPC ............ 422/72; 422/400; 422/209; 422/502; 422/506; 422/537
(58) Field of Classification Search
USPC .................. 422/72, 209, 400; 436/45, 177
See application file for complete search history.

(56) References Cited

U.S. PATENT DOCUMENTS

| | | | | |
|---|---|---|---|---|
| 5,286,454 A | * | 2/1994 | Nilsson et al. | 422/548 |
| 2004/0028558 A1 | | 2/2004 | Pollock et al. | 422/57 |
| 2004/0120856 A1 | * | 6/2004 | Andersson et al. | 422/72 |
| 2004/0129678 A1 | | 7/2004 | Crowley et al. | 216/84 |

FOREIGN PATENT DOCUMENTS

| | | |
|---|---|---|
| EP | 0 287 883 | 10/1988 |
| EP | 1 508 373 | 2/2005 |
| JP | 2005-114438 | 4/2005 |
| WO | WO 90/13016 A1 | 11/1990 |
| WO | WO 02/074438 A2 | 10/2002 |
| WO | 2005/116662 | 12/2005 |
| WO | 2005/119211 | 12/2005 |
| WO | 2007/042207 | 4/2007 |

* cited by examiner

*Primary Examiner* — Sally Merkling
(74) *Attorney, Agent, or Firm* — Steptoe & Johnson LLP

(57) ABSTRACT

A microchip having an inlet (14) for collecting a liquid sample; at least one capillary cavity (4) capable of collecting a specific amount of the liquid sample through the inlet (14) by using capillary force; and a holding chamber (5) communicating with the capillary cavity (4) and receiving the sample liquid in the capillary cavity (4) transferred by centrifugal force generated by rotation about an axis. The capillary cavity (4) interconnecting the inlet (14) and the holding chamber (5) has, in one side face of the capillary cavity (4), cavities (15, 16) not generating capillary force and communicating with the atmosphere, and this prevents mixing of air bubbles into the capillary cavity (4).

7 Claims, 12 Drawing Sheets

MICROCHIP AND ANALYZER USING THE SAME

This application is a national stage entry of International Application No. PCT/JP2007/070603, filed Oct. 23, 2007 designating the U.S., which claims the benefit of Japanese Application No. 2006-295159, filed Oct. 31, 2006.

TECHNICAL FIELD

The present invention relates to a microchip for electrochemically or optically analyzing a biological fluid.

BACKGROUND ART

As a conventional method of electrochemically analyzing a biological fluid using a microchip, a biosensor for analyzing a specific component in a liquid sample obtains, for example, a blood glucose level and so on by measuring a current value obtained from the reaction of glucose in blood and a reagent, such as glucose oxidase, supported in the sensor.

As a method of optically analyzing a biological fluid, a method of analyzing a biological fluid using a microchip having liquid channels formed thereon is known. This microchip, capable of controlling a fluid using a rotary device having a horizontal shaft, can weigh liquid samples, separate cytoplasmic materials, transfer and distribute the separated fluids, mix/stir liquids, and the like, by using centrifugal force. This makes it possible to perform a variety of biochemical analyses.

As a conventional method of collecting a liquid sample, a centrifugal transfer biosensor, shown in FIG. 12, is disclosed in Patent Document 1. This centrifugal transfer biosensor has a plurality of cavities having different depths formed in a container 310. A liquid sample is collected into a first capillary cavity 312 through an inlet 313 by capillary action, and then the liquid sample in the first capillary cavity 312 is transferred to a receiving cavity 317 through a filtering material 315 and a first channel 314 under the action of centrifugal force. Then, after the liquid sample reacts with a reagent and is centrifuged in the receiving cavity 317, only a solution component of the liquid sample is collected in a second capillary cavity 316 by the capillary force of a core 318, and the reaction state of the liquid sample is read optically.

Further, another centrifugal transfer biosensor, shown in FIG. 13, is disclosed in Patent Document 2. FIG. 13 shows a distribution unit 400. An inlet port 409 is connected to a capillary cavity 404a through an upper part 402. The capillary cavity 404a is connected to a capillary cavity 404b through a conduit 405a. Similarly, the capillary cavity 404 band capillary cavities 404c, 404d, 404e, and 404f are connected sequentially through conduits 405b, 405c, 405d, and 405e. The capillary cavity 404f is connected to an outlet port 410 through an upper part 403. Air vents 406a, 406b, 406c, 406d, 406e, 406f, and 406g are provided at the upper part 402, the conduits 405a, 405b, 405c, 405d, and 405e, and the upper part 403, respectively. A liquid sample introduced through the inlet port 409 is transferred to the outlet port 410 by capillary force to fill the capillary cavities 404a, 404b, 404c, 404d, 404e, and 404f with the liquid sample. By centrifugal force generated by the rotation of the biosensor, the liquid sample in the capillary cavities 404a, 404b, 404c, 404d, 404e, and 404f is then distributed at the air vents 406a, 406b, 406c, 406d, 406e, 406f, and 406g, and is transferred to a subsequent treatment chamber (not shown) through valves 408a, 408b, 408c, 408d, 408e, and 408f and connecting microconduits 407a, 407b, 407c, 407d, 407e, and 407f, correspondingly.

Patent Document 1: Japanese Unexamined Patent Application Publication (Translation of PCT Application) No. 4-504758
Patent Document 2: Japanese Unexamined Patent Application Publication (Translation of PCT Application) No. 2004-529333

DISCLOSURE OF THE INVENTION

Problems to be Solved by the Invention

However, with the foregoing conventional structures, a liquid sample may not be supplied in sufficient quantities to fill capillary cavities, or when a liquid sample is separated from the inlet during the application of a droplet thereof, air bubbles may form due to the surface tension near the inlet. Further, when the orientation of the device is changed while handling after a liquid sample is introduced, the liquid sample in the capillary cavity moves, so that air bubbles may form.

Once such air bubbles have formed, it becomes impossible to expel the air bubbles from the capillary cavity in order to draw an additional liquid sample thereinto to make up for the shortage. As a result, it is impossible to fill parts of the air bubbles with a liquid sample, and therefore it is impossible to collect a specific amount of liquid sample.

To solve the conventional problems described above, it is an object of the present invention to provide a microchip which can prevent air bubbles from forming in a capillary cavity and thus collect a liquid sample any number of times until the capillary cavity is full.

Solution to the Problems

According to a first aspect of the present invention, a microchip includes: an inlet for collecting a liquid sample therethrough; at least one capillary cavity capable of collecting a specific amount of the liquid sample through the inlet by capillary force; and a holding chamber that communicates with the capillary cavity and that receives the liquid sample transferred from the capillary cavity by centrifugal force generated by rotation about an axis. A cavity is provided to one side face of the capillary cavity connecting the inlet with the holding chamber, the cavity communicating with the atmosphere without generating capillary force.

According to a second aspect of the present invention, a microchip includes: a storage chamber for storing a liquid sample; at least one capillary cavity capable of collecting a specific amount of the liquid sample from the storage chamber by capillary force; and a holding chamber that communicates with the capillary cavity and that receives the liquid sample transferred from the capillary cavity by centrifugal force generated by rotation about an axis. A cavity is provided to one side face of the capillary cavity connecting the storage chamber with the holding chamber, the cavity communicating with the atmosphere without generating capillary force.

According to a third aspect of the present invention, in the microchip according to one of the first aspect and the second aspect, cross-sectional shapes of the capillary cavity and the cavity are rectangular; the cavity is greater in cross-sectional size in a thickness direction than the capillary cavity; and the cavity is formed to one side or opposite sides of the capillary cavity.

According to a fourth aspect of the present invention, in the microchip according to one of the first aspect and the second aspect, a portion of a cross section of the capillary cavity is arc-shaped; a cross section of the cavity is rectangular; the cavity is greater in cross-sectional size in a thickness direction than the capillary cavity; and the cavity is formed to one side or opposite sides of the capillary cavity.

According to a fifth aspect of the present invention, in the microchip according to one of the third aspect and the fourth aspect, the cavity is at least 50 µm greater in cross-sectional size in the thickness direction than the capillary cavity.

According to a sixth aspect of the present invention, in the microchip according to one of the first aspect and the second aspect, portions of cross sections of the capillary cavity and the cavity are arc-shaped; and the cavity is formed to one side or opposite sides of the capillary cavity.

According to a seventh aspect of the present invention, in the microchip according to one of the first aspect and the second aspect, a wall of the cavity is a hydrophobic surface.

According to an eighth aspect of the present invention, a microchip includes: an inlet for collecting a liquid sample therethrough; a first capillary cavity that communicates with the inlet and can collect a specific amount of the liquid sample through the inlet by capillary force; a first holding chamber that communicates with an outer peripheral end of the first capillary cavity and receives the liquid sample transferred from the first capillary cavity by centrifugal force generated by rotation about an axis; a second capillary cavity that communicates with the first capillary cavity and can collect a specific amount of the liquid sample through the first capillary cavity by capillary force; and a second holding chamber that communicates with an outer peripheral end of the second capillary cavity and that receives the liquid sample transferred from the second capillary cavity by the centrifugal force generated by the rotation about the axis. A cavity is provided to one side face of each of the first capillary cavity and the second capillary cavity, the cavity communicating with the atmosphere without generating capillary force; a boundary between the first capillary cavity and the second capillary cavity has a curved shape, projecting in an inner peripheral direction, on an inner peripheral side with respect to the first holding chamber and the second holding chamber; and the boundary has a wall on the outer peripheral side.

According to a ninth aspect of the present invention, a microchip includes: an inlet for collecting a liquid sample therethrough; a first capillary cavity that communicates with the inlet and can collect a specific amount of the liquid sample through the inlet by capillary force; a first holding chamber that communicates with an outer peripheral end of the first capillary cavity and receives the liquid sample transferred from the first capillary cavity by centrifugal force generated by rotation about an axis; a second capillary cavity that communicates with the first capillary cavity and can collect a specific amount of the liquid sample through the first capillary cavity by capillary force; a second holding chamber that communicates with an outer peripheral end of the second capillary cavity and that receives the liquid sample transferred from the second capillary cavity by the centrifugal force generated by the rotation about the axis; N−2 capillary cavities that are formed in contiguous communication with one another from the second capillary cavity to the Nth (N is a positive integer equal to or greater than 3) capillary cavity; and N−2 holding chambers that communicate with outer peripheral ends of the respective N−2 capillary cavities and that receive the liquid sample transferred from the respective N−2 capillary cavities by the centrifugal force generated by the rotation about the axis. A cavity is provided to one side face of each of the first capillary cavity, the second capillary cavity, and the N−2 capillary cavities formed contiguously from the second capillary cavity to the Nth capillary cavity, the cavity communicating with the atmosphere without generating capillary force; a boundary between the first capillary cavity and the second capillary cavity has a curved shape, projecting in an inner peripheral direction, on an inner peripheral side with respect to the first holding chamber and the second holding chamber; N−2 boundaries of the respective N−2 capillary cavities formed contiguously from the second capillary cavity to the Nth capillary cavity each have a curved shape, projecting in an inner peripheral direction, on an inner peripheral side with respect to the N−2 holding chambers from the second holding chamber to the Nth holding chamber; and N−1 boundaries from a first boundary to an N−1th boundary each have a wall on the outer peripheral side.

According to a tenth aspect of the present invention, a microchip includes: a storage chamber for storing a liquid sample; a fourth capillary cavity that communicates with the storage chamber and can collect a specific amount of the liquid sample from the storage chamber by capillary force; a fourth holding chamber that communicates with an outer peripheral end of the fourth capillary cavity and that receives the liquid sample transferred from the fourth capillary cavity by centrifugal force generated by rotation about an axis; a fifth capillary cavity that communicates with the fourth capillary cavity and can collect a specific amount of the liquid sample through the fourth capillary cavity by capillary force; and a fifth holding chamber that communicates with an outer peripheral end of the fifth capillary cavity and that receives a liquid sample transferred from a second capillary cavity by the centrifugal force generated by the rotation about the axis. A cavity is provided to one side face of each of the fourth capillary cavity and the fifth capillary cavity, the cavity communicating with the atmosphere without generating capillary force; a boundary between the fourth capillary cavity and the fifth capillary cavity has a curved shape, projecting in an inner peripheral direction, on an inner peripheral side with respect to the storage chamber and the fourth holding chamber; and the boundary has a wall on the outer peripheral side.

According to an eleventh aspect of the present invention, a microchip includes: a storage chamber for storing a liquid sample; a second capillary cavity that communicates with the storage chamber and can collect a specific amount of the liquid sample from the storage chamber by capillary force; a second holding chamber that communicates with an outer peripheral end of the second capillary cavity and that receives the liquid sample transferred from the second capillary cavity by centrifugal force generated by rotation about an axis; a third capillary cavity that communicates with the second capillary cavity and can collect a specific amount of the liquid sample through the second capillary cavity by capillary force; a third holding chamber that communicates with an outer peripheral end of the third capillary cavity and that receives the liquid sample transferred from the third capillary cavity by the centrifugal force generated by the rotation about the axis; N−2 capillary cavities that are formed in contiguous communication with one another from the third capillary cavity to the Nth (N is a positive integer equal to or greater than 3) capillary cavity; and N−2 holding chambers that communicate with outer peripheral ends of the respective N−2 capillary cavities and that receive the liquid sample transferred from the respective N−2 capillary cavities by the centrifugal force generated by the rotation about the axis. A cavity is provided to one side face of each of the second capillary cavity, the third capillary cavity, and the N−2 capillary cavities formed contiguously from the third capillary cavity to the Nth capillary cavity, the cavity communicating with the atmosphere without generating capillary force; a second boundary between the second capillary cavity and the third capillary cavity has a curved shape, projecting in an inner peripheral direction, on an inner peripheral side with respect to the second capillary cavity and the third capillary cavity; N−2 boundaries of the respective N−2 capillary cavities formed contiguously from the third capillary cavity to the Nth capillary cavity each have a curved shape, projecting in an inner peripheral direction, on an inner peripheral side with respect to the N−2 holding chambers from the third holding chamber to the Nth holding chamber; and N−1 boundaries from the second boundary to the N−1th boundary each have a wall on the outer peripheral side.

According to a twelfth aspect of the present invention, an analyzer having mounted thereon the microchip according to the first aspect, includes: rotary drive means for rotating the microchip about the axis while holding the microchip with the inlet directed toward the axis; and analysis means for analyzing the liquid sample in the holding chamber after the rotary drive means transfers the liquid sample, collected through the inlet and held in the capillary cavity, to the holding chamber. The analyzer collects the liquid sample through the inlet of the microchip until the capillary cavity is full and then transfers the liquid sample from the capillary cavity to the holding chamber through the cavity and the cavity that does not contain the liquid sample, by the centrifugal force generated by the rotation of the microchip by the rotary drive means.

According to a thirteenth aspect of the present invention, an analyzer having mounted thereon the microchip according to the second aspect, includes: rotary drive means for rotating the microchip about the axis; and analysis means for analyzing a liquid sample in the holding chamber after the rotary drive means transfers the liquid sample, collected from the storage chamber and held in the capillary cavity, to the holding chamber. The analyzer collects the liquid sample from the storage chamber until the capillary cavity is full and then transfers the liquid sample from the capillary cavity to the holding chamber through the cavity and the cavity that does not contain the liquid sample, by the centrifugal force generated by the rotation of the microchip by the rotary drive means.

Effect of the Invention

A microchip of the present invention can prevent air bubbles from forming in a capillary cavity that collects a liquid sample, and therefore can collect the liquid sample any number of times until the capillary cavity is full. This makes it possible to eliminate measurement errors due to deficiencies in the collection of the liquid sample and therefore improve the measurement accuracy of the microchip.

BEST MODE FOR CARRYING OUT THE INVENTION

With reference to FIG. 1 through FIG. 11 and FIG. 14, each embodiment of the present invention will be described below.

Embodiment 1

FIG. 1 through FIG. 8 show Embodiment 1 of the present invention.

Figure 1:
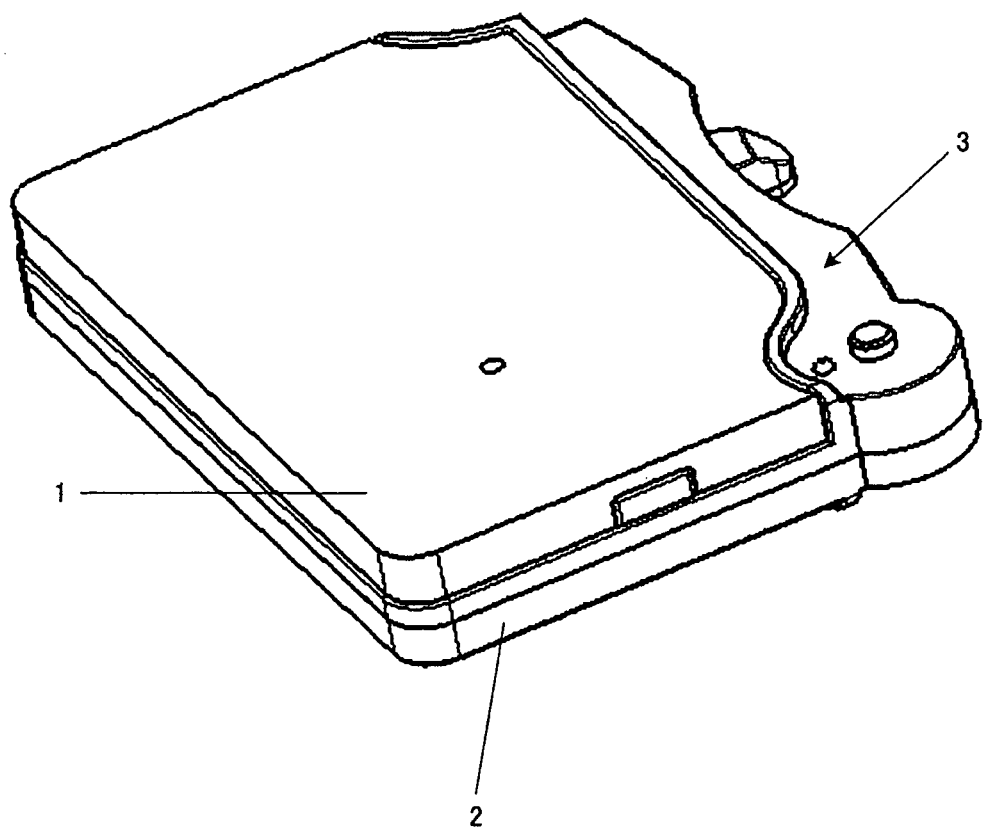
FIG. 1 is an external view of a microchip according to Embodiment 1 of the present invention.
Figure 2:
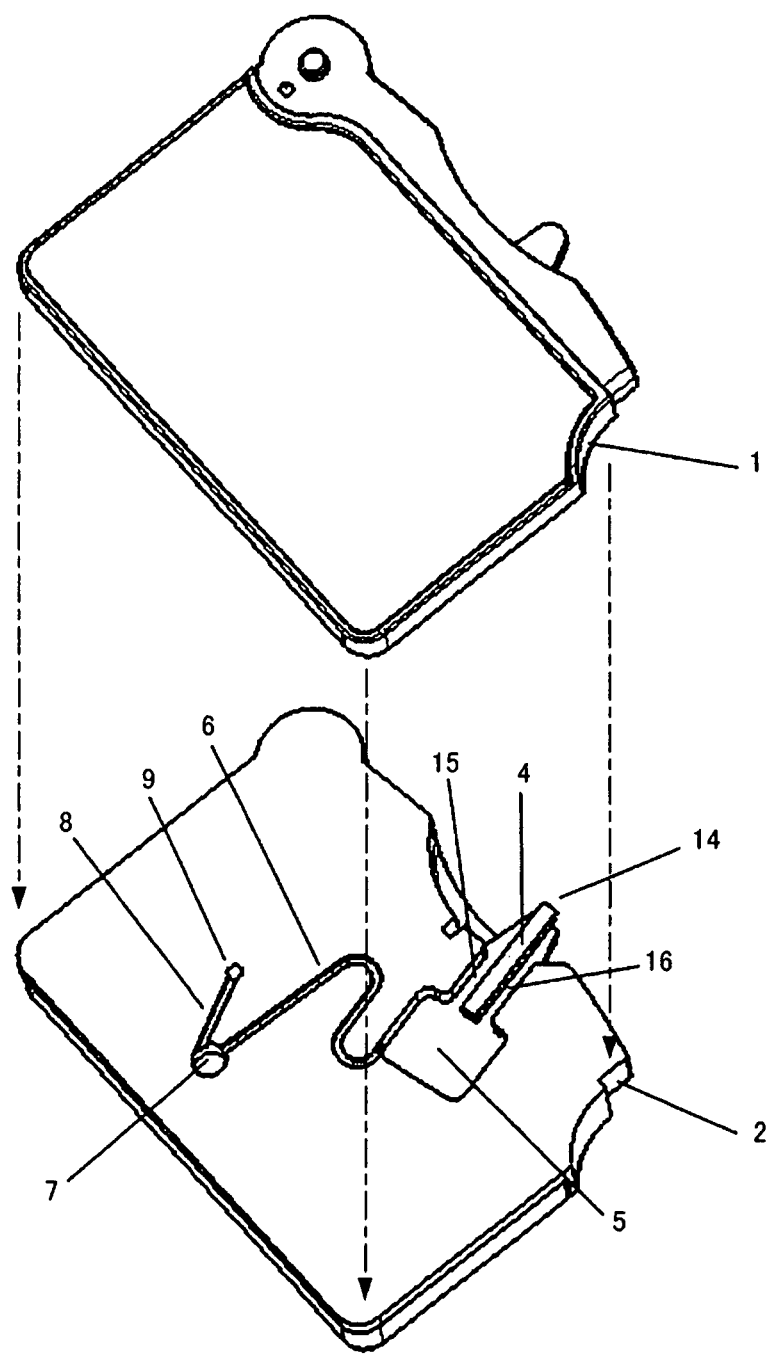
FIG. 2 is an exploded perspective view of the microchip according to Embodiment 1.

FIG. 1 is an external view of a microchip 3. FIG. 2 is an exploded perspective view of the structure of the microchip 3. The microchip 3 is constructed by bonding a top substrate 1 and a bottom substrate 2. On one surface of the bottom substrate 2, a microchannel structure having a micro-concavo-convex shape is formed so as to perform functions such as transferring a liquid sample and holding a predetermined amount of fluid.

Figure 3:
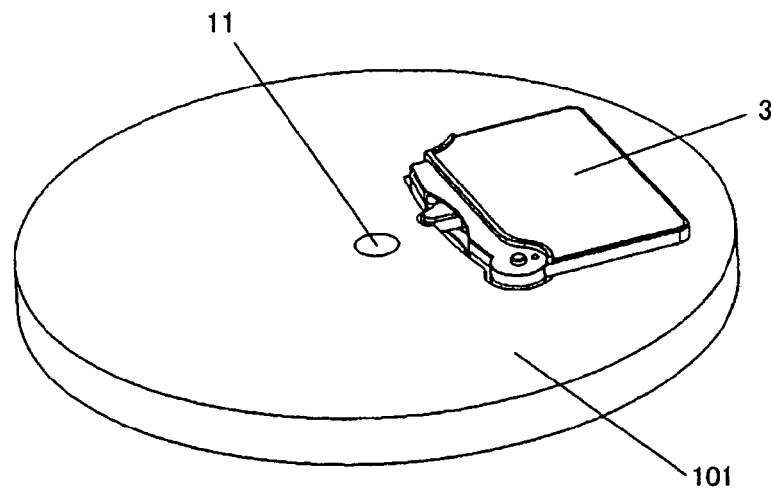
FIG. 3 is an external perspective view showing the state of the microchip of Embodiment 1 attached to a microchip holding member.

FIG. 3 is an external perspective view showing the state of the microchip 3 attached to a microchip holding member 101. In this case, one microchip 3 is attached to the microchip holding member 101 so that rotary drive means provided in an analyzer (not shown) rotates the microchip holding member 101 and the microchip 3 in a predetermined direction about an axis 11.

Figure 4:
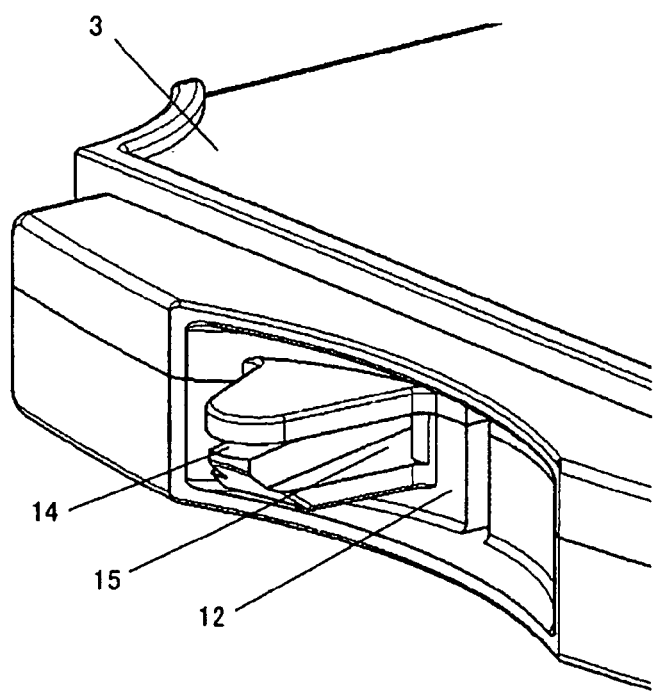
FIG. 4 is an enlarged perspective view of the periphery of an inlet according to Embodiment 1.

FIG. 4 is an enlarged view of the periphery of an inlet 14 of the microchip 3. As shown in FIG. 4, the inlet 14 protrudes beyond one side surface of the microchip body toward the axis 11. This makes it easy to apply a droplet to the inlet 14 with a fingertip or the like, and therefore prevents, when a finger or the like contacts positions other than the inlet 14 while applying a droplet of blood, the blood from adhering to the positions.

In the periphery of the inlet 14, the one side surface of the microchip 3 has formed thereon a concave portion 12, which is open to only the axis 11 side and is depressed in the outer peripheral direction from the axis 11. Note that, in the present embodiment, the concave portion 12 is gently curved in such a manner that, in the opening of the concave portion, the cross-sectional area on the axis side is equal to or greater than that on the outer peripheral side. This makes it possible that, when centrifugal force is applied, a liquid sample adhering to the periphery of the inlet 14 is transferred to the concave portion with certainty, and also is easily transferred to the lowest position of the concave portion. Thus, the liquid sample can be collected without spattering out of the concave portion.

Note that, with a protrusion formed so that the inlet 14 protrudes from the bottom surface of this open concave portion 12 toward the axis 11, the liquid sample adhering to the periphery of the inlet 14 is transferred into the concave portion. At this time, the position into which the liquid sample is transferred is virtually the bottom surface of the concave portion. Thus, the liquid sample can be stably collected without flowing out of the concave portion, and can also be collected by one concave portion.

Figure 5:
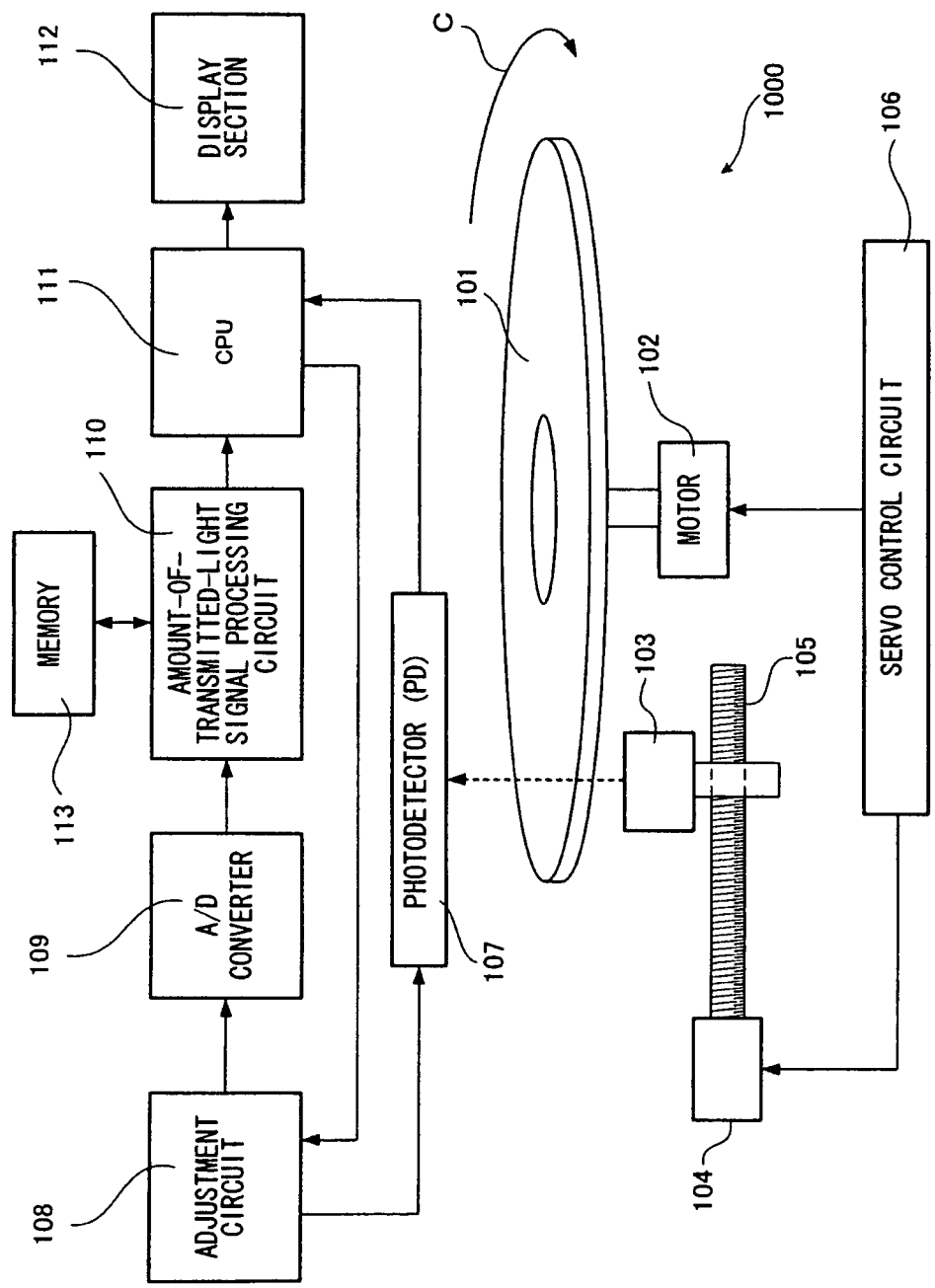
FIG. 5 is a diagram showing the structure of an analyzer according to Embodiment 1.

FIG. 5 is a schematic diagram showing the structure of an analyzer 1000 on which the microchip 3 of Embodiment 1 is mounted. Referring to FIG. 5, the microchip 3 is attached to the top side of the microchip holding member 101 attached to the rotary shaft of a motor 102, which is the rotary drive means of the analyzer 1000, such that the microchip holding member 101 having the microchip 3 attached thereto can be rotationally driven about the axis by rotationally driving the motor 102.

By arranging chambers and channels in the microchip 3 depending on the intended use, the analyzer can also act as a centrifuge that transfers and centrifuges a liquid in the microchip, using the centrifugal force generated by the rotation about the axis. Note that the microchip 3, mounted on the analyzer 1000 in the present invention, may have another shape such as a fan or cubic shape. Alternatively, a plurality of microchips 3 may be simultaneously mounted on the analyzer 1000.

The analyzer 1000 causes laser light from a laser source 103 to be irradiated on the microchip attached to the microchip holding member 101 of the analyzer, while rotationally driving the microchip holding member 101 by the motor 102 in a direction C. The laser source 103 is screwed to a feed screw 105, which is driven by a traverse motor 104, and therefore can be moved in the radial direction of the microchip holding member 101 by driving the traverse motor 104 so that a servo control circuit 106 can place the laser source 103 at any measurement position.

Above the microchip holding member 101, the following are provided: a photodetector (PD) 107 for detecting, of the laser light emitted from the laser source 103, the amount of transmitted light passed through the microchip holding member 101; an adjustment circuit 108 for adjusting the gain of the output of the photodetector (PD) 107; an A/D converter 109 for digitally converting the output of the adjustment circuit 108; an amount-of-transmitted-light signal processing circuit 110 for processing the data obtained by the digital conversion of the A/D converter 109; a memory 113 for storing the data obtained by the amount-of-transmitted-light signal processing circuit 110; a microcomputer (CPU) 111 for controlling these elements; and a display section 112 for displaying an analyzed result.

Note that, in the present embodiment, an optical scanning technique for an optical disk is not particularly used. However, the irradiation from the laser source 103 on the microchip 3 may be performed in such a manner that the microchip 3 includes a region having recorded therein position information whereby a tracking actuator (not shown) provided in the laser source 103, as well as the drive of the traverse motor 104, traces the track of the microchip with accuracy while driving and positionally controlling the optical path of the laser light in the surface direction of the microchip, where necessary.

Next, the microchannel structure of the microchip 3 of Embodiment 1 and the transfer process of a liquid sample will be described in detail.

Figure 6:
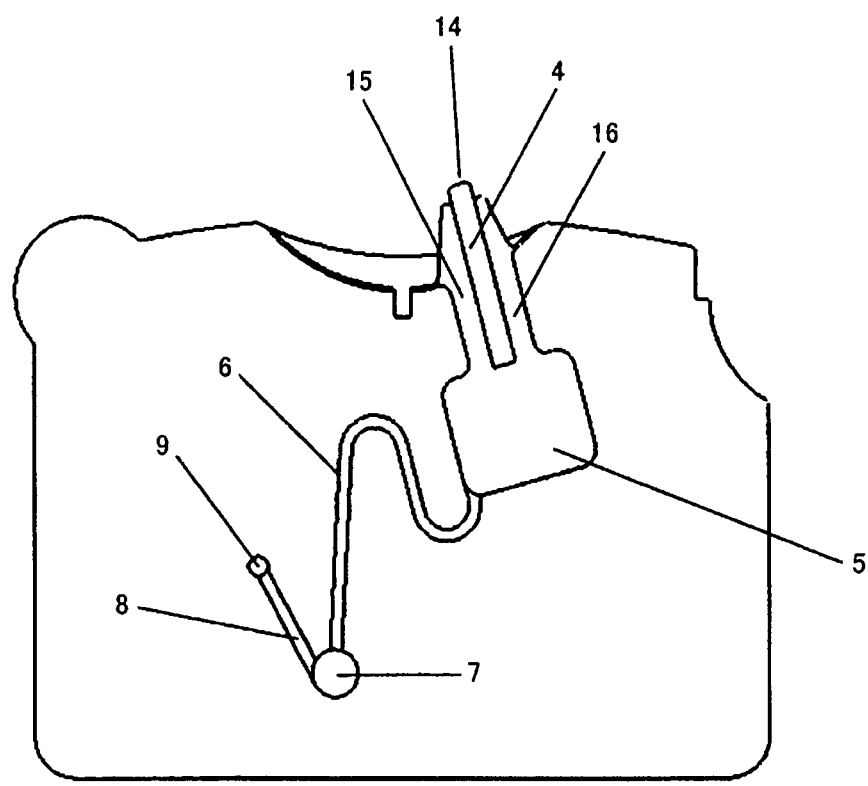
FIG. 6 is a plan view of a microchannel structure according to Embodiment 1.
Figure 7A:
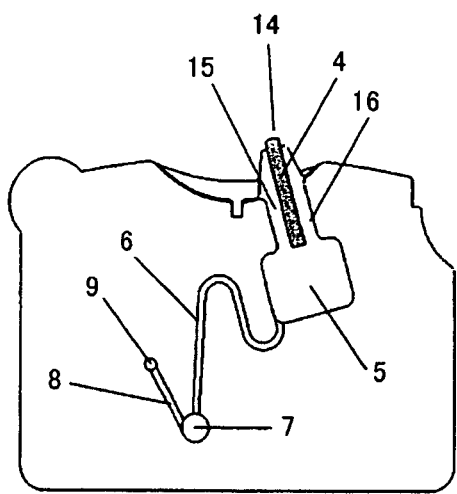
FIG. 7A to FIG. 7D are diagrams each illustrating a "liquid sample introduction process" through to a "measuring chamber filling process", of Embodiment 1.

FIG. 6 is a plan view of the microchannel structure of the microchip of Embodiment 1. FIG. 7 is a diagram illustrating a "microchip liquid sample introduction process" through to a "measuring chamber filling process", of Embodiment 1. FIG. 8A to FIG. 8F show examples of the cross-sectional shapes of a capillary cavity and cavities of the microchip. FIG. 8A is a cross-sectional view showing the case where the cross-sectional shapes of a capillary cavity 4 and cavities 15 and 16 of the present embodiment are rectangular. FIG. 8B is a cross-sectional view showing the case where the cross-sectional shapes of the capillary cavity 4 and the cavity 15 of the present embodiment are arc-shaped. FIG. 8C is a cross-sectional view showing the case where the cross-sectional shape of the capillary cavity 4 of the present embodiment is arc-shaped and the cross-sectional shape of the cavity 15 of the present embodiment is rectangular. FIG. 8D is a cross-sectional view showing the case where the cross-sectional shapes of the capillary cavity 4 and the cavities 15 and 16 of the present embodiment are rectangular, of the same thickness. FIG. 8E is a cross-sectional view showing the case where the cross-sectional shapes of the capillary cavity 4 and the cavities 15 and 16 of the present embodiment are rectangular and the cavities 15 and 16 are thicker than the capillary cavity 4. FIG. 8F is a cross-sectional view showing the case where the cross-sectional shapes of the capillary cavity 4 and the cavity 15 of the present embodiment are arc-shaped and the cavity 15 is thicker than the capillary cavity 4.

As shown in FIG. 6, the microchannel structure of the microchip 3 of Embodiment 1 includes: an inlet 14 for collecting a liquid sample therethrough; a capillary cavity 4 for holding a predetermined amount of the liquid sample introduced into the inlet 14; cavities 15 and 16 for expelling the air from the capillary cavity 4; a holding chamber 5 having an analytical reagent (not shown) held therein; a measuring chamber 7 for measuring the mixture of the liquid sample and the analytical reagent; a channel 6 communicating with the holding chamber 5 and the measuring chamber 7; and a channel 8 connecting the measuring chamber 7 with an atmospheric vent 9. Here in the present invention, the capillary cavity 4, the channel 6, and the channel 8 are formed with depths of 50 μm to 300 μm, but may not be limited to these sizes so long as the liquid sample can flow through each element by capillary force. Further, the holding chamber 5, the measuring chamber 7, and the cavities 15 and 16 are formed with depths of 0.3 mm to 5 mm, but these depths can be adjusted in accordance with the amount of sample solution, and the conditions of absorbance measurements (an optical path length, a measurement wavelength, the reaction concentration of the sample solution, the type of a reagent, etc.).

In Embodiment 1, the walls of the capillary cavity 4, the channel 6, and the channel 8 are subjected to a hydrophilic treatment so that the liquid sample can flow through each element by capillary force. The hydrophilic treatment method may include a surface treatment method that uses active gas such as plasma, corona, ozone, and fluorine, and may also include a surface treatment by a surface active agent and a hydrophilic polymer. Here, hydrophilicity is obtained when the contact angle with water is less than 90°, and more preferably less than 40°.

Next, with reference to FIG. 7, the transfer process of a liquid sample will be described in detail. First, in order to supply the liquid sample to the microchip 3 having this structure, a droplet of the liquid sample is applied to the inlet 14, which protrudes from the one side surface of the microchip 3 toward the axis 11, when the microchip 3 is detached from the microchip holding member 101. Immediately after the droplet is applied, a predetermined amount of the liquid sample is introduced into the capillary cavity 4 by capillary action as shown in FIG. 7A.

At this time, in the present invention, the cavities 15 and 16 are provided to the sides of the capillary cavity 4, so as to expel the air from the capillary cavity 4. Thus, the capillary flow of the liquid sample filling the capillary cavity 4 flows ahead not in the side portion of the capillary cavity 4, but in the center portion of the capillary cavity 4. Consequently, even when the liquid sample to be applied as a droplet to the inlet 14 runs short while filling the capillary cavity 4, or even when the liquid sample is separated from the inlet 14 while filling the capillary cavity 4, another droplet may be reapplied to the inlet, so that the reapplied liquid sample flows ahead in the center portion of the capillary cavity 4, and therefore contacts the center portion of the liquid sample held in the capillary cavity and fills the capillary cavity while expelling the air in the directions of the sides on which the cavities 15 and 16 are provided. As a result, air bubbles are not produced, and droplets can be applied any number of times until the capillary cavity 4 can hold a predetermined amount of the liquid sample.

The arrangements of the capillary cavity 4 and the cavities 15 and 16 may include: an arrangement as shown in FIG. 8A in which either or both of the cavities 15 and 16, each having a greater section size in the thickness direction than that of the capillary cavity 4, are provided to one side or opposite sides of the rectangular capillary cavity 4 formed on the bottom substrate; an arrangement as shown in FIG. 8B in which either or both of the arc-shaped cavities 15 and 16 are provided to one side or opposite sides of the arc-shaped capillary cavity 4 formed on the bottom substrate; an arrangement as shown in FIG. 8C in which either or both of the rectangular cavities 15 and 16, each having a greater section size in the thickness direction than that of the capillary cavity 4, are provided to one side or opposite sides of the arc-shaped capillary cavity 4 formed on the bottom substrate; an arrangement as shown in FIG. 8D in which either or both of the rectangular cavities 15 and 16, each having the same section size in the thickness direction as that of the capillary cavity 4, are provided to one side or opposite sides of the rectangular capillary cavity 4 formed on the bottom substrate and the walls of the cavities 15 and 16 are hydrophobic surfaces or are subjected to a hydrophobic treatment (as a hydrophobicity standard, the contact angle with water is preferably 90° or larger, but may be 70° or larger); an arrangement as shown in FIG. 8E in which either or both of the cavities 15 and 16 are provided, across both the bottom and top substrates, to one side or opposite sides of the rectangular capillary cavity 4 formed on the bottom substrate so that the cavities 15 and 16 each have a greater section size in the thickness direction than that of the capillary cavity 4; and an arrangement as shown in FIG. 8F in which either or both of the arc-shaped cavities 15 and 16 are provided, across both the bottom and top substrates, to one side or opposite sides of the arc-shaped capillary cavity 4 formed across both the bottom and top substrates. However, the arrangement of the capillary cavity and the cavities of the present invention may not be limited to these arrangements.

In the arrangements shown in FIGS. 8A, 8C and 8E, the cross-sectional sizes of the cavities 15 and 16 in the thickness direction are each made at least 50 µm greater than that of the capillary cavity 4. This makes it possible to prevent the liquid sample from flowing into the cavities 15 and 16. There is no particular rule for the upper limit of the cross-sectional sizes of the cavities 15 and 16 in the thickness direction. However, since it is necessary to provide the top substrate 1 with rigidity so as to maintain the cross-sectional size of the capillary cavity in the thickness direction, a distance of about 0.5 mm to 1 mm is preferably maintained between the top surface of the top substrate 1 and the cavities 15 and 16. Additionally, it is necessary to perform a hydrophilic treatment on the capillary cavity 4 so as to cause capillary action therein. The hydrophilic treatment is preferably performed only on the wall of the capillary cavity 4. If a hydrophilic treatment is performed also on the walls of the cavities 15 and 16, the liquid sample is likely to flow into these cavities.

Figure 7B:
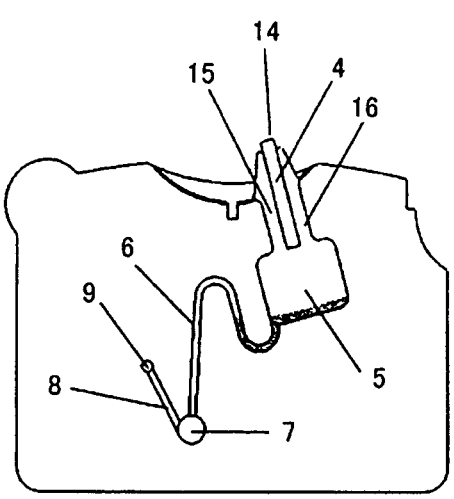
Figure 8A:
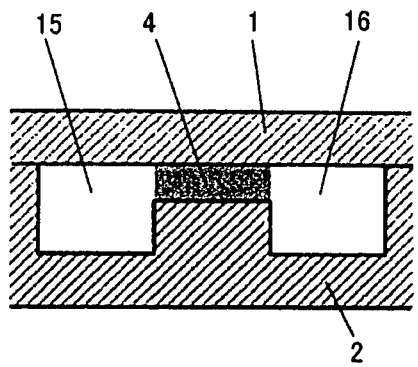
FIG. 8A to FIG. 8F are diagrams each showing the cross-sectional shapes of a capillary cavity and cavities of the microchip according to Embodiment 1 of the present invention.
Figure 8B:
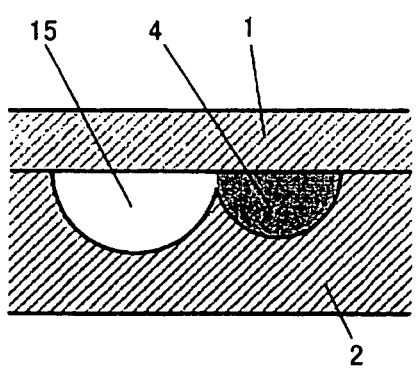
Figure 8C:
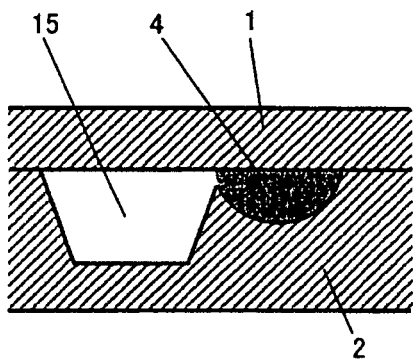
Figure 8D:
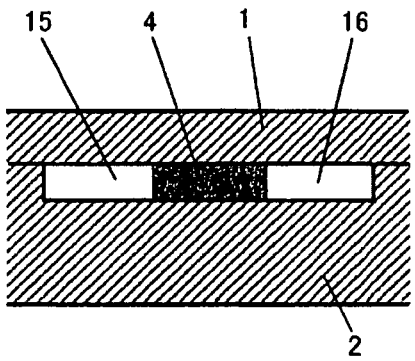
Figure 8E:
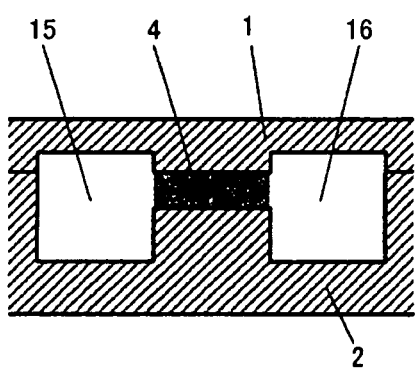
Figure 8F:
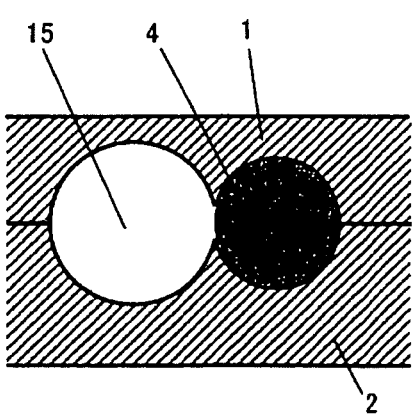

After the capillary cavity 4 is filled with the liquid sample, the microchip 3 is mounted on the analyzer 1000 and is rotated by the rotary drive means of the analyzer 1000, whereby the liquid sample in the capillary cavity 4 is transferred by centrifugal force into the holding chamber 5, which holds the analytical reagent in advance, as shown in FIG. 7B.

The liquid sample having flowed into the holding chamber 5 is mixed with the analytical reagent held in the holding chamber 5, by vibrations due to the acceleration of the rotation of the analyzer 1000 or by the diffusion of the liquid while the rotation is stopped, but can also be mixed under the action of an external force that directly vibrates the holding chamber 5 per se.

Figure 7C:
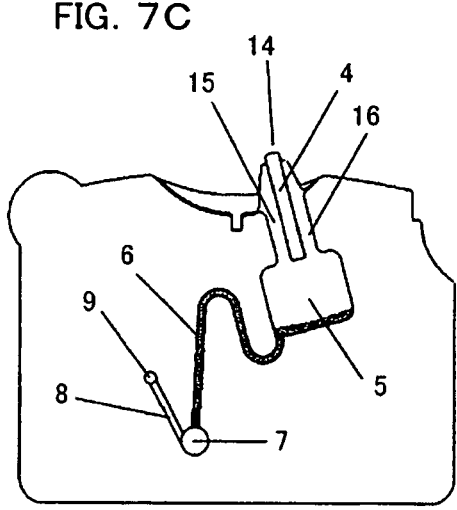

Next, when the mixture of the reagent and the liquid sample reaches a predetermined level, the liquid sample in the holding chamber 5 is transferred by capillary force to the inlet of the measuring chamber 7 through the channel 6, as shown in FIG. 7C.

Figure 7D:
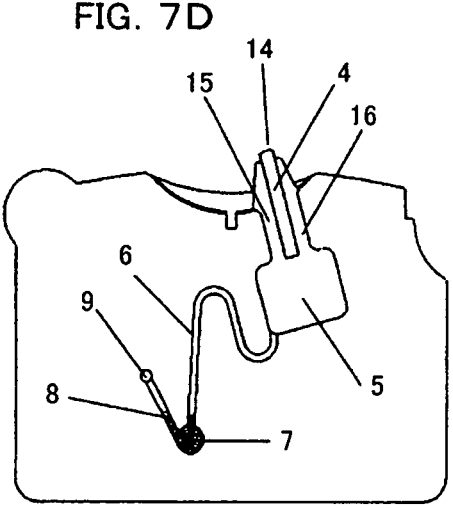

Next, the liquid sample in the channel 6 is transferred into the measuring chamber 7 by the rotation of the analyzer 1000, as shown in FIG. 7D. Then, the analyzer 1000 measures the reaction state of the liquid sample and the analytical reagent by absorbance measurement and the like, whereby it is possible to measure the concentration of a component of the liquid sample.

Embodiment 2

Figure 9:
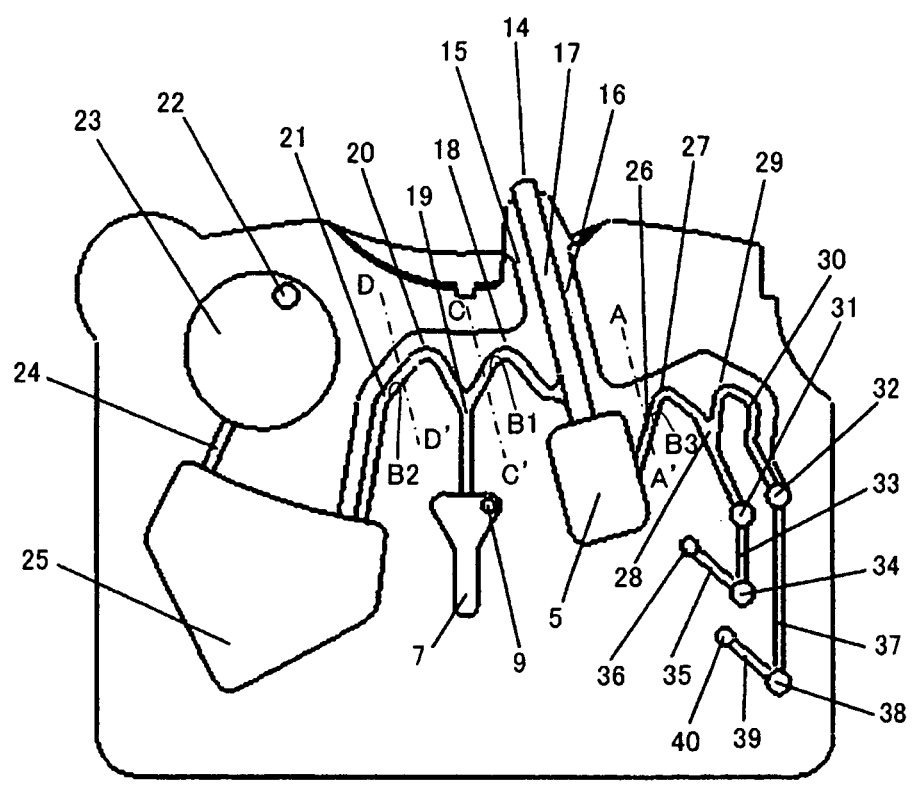
FIG. 9 is a plan view of a microchip according to Embodiment 2 of the present invention.
Figure 10A:
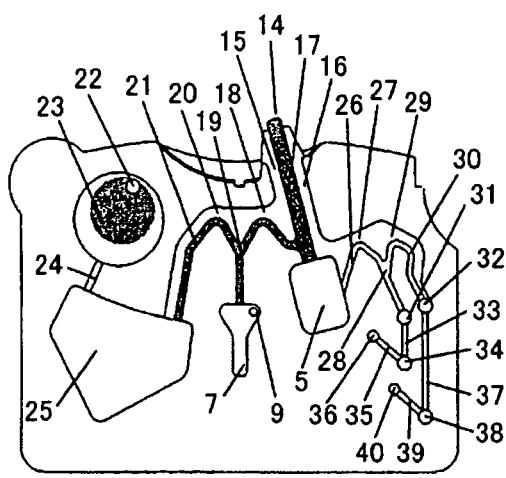
FIG. 10A to FIG. 10D are diagrams each illustrating a "liquid sample introduction process" through to a "measuring chamber filling process", of Embodiment 2.
Figure 10B:
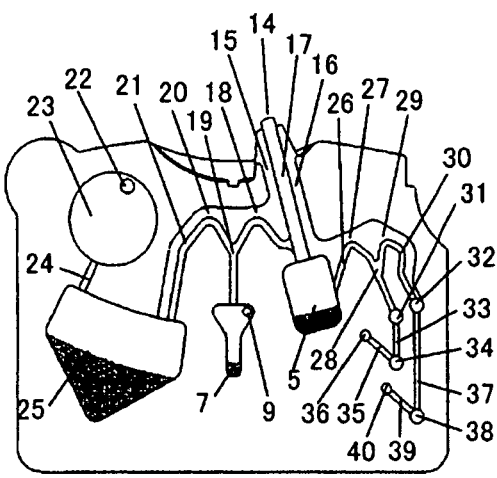
Figure 10C:
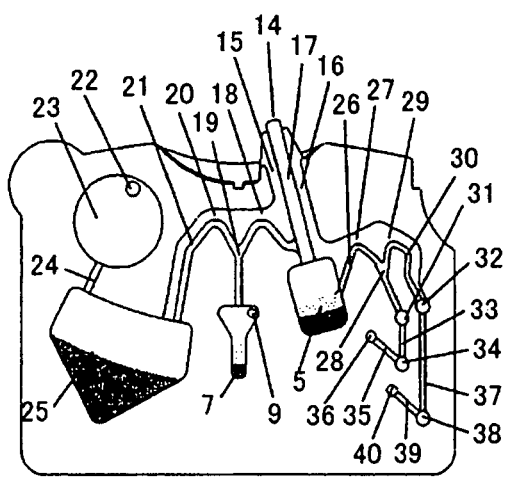
Figure 10D:
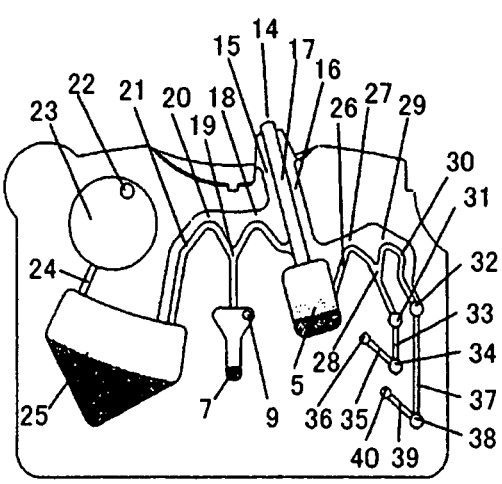
Figure 11:
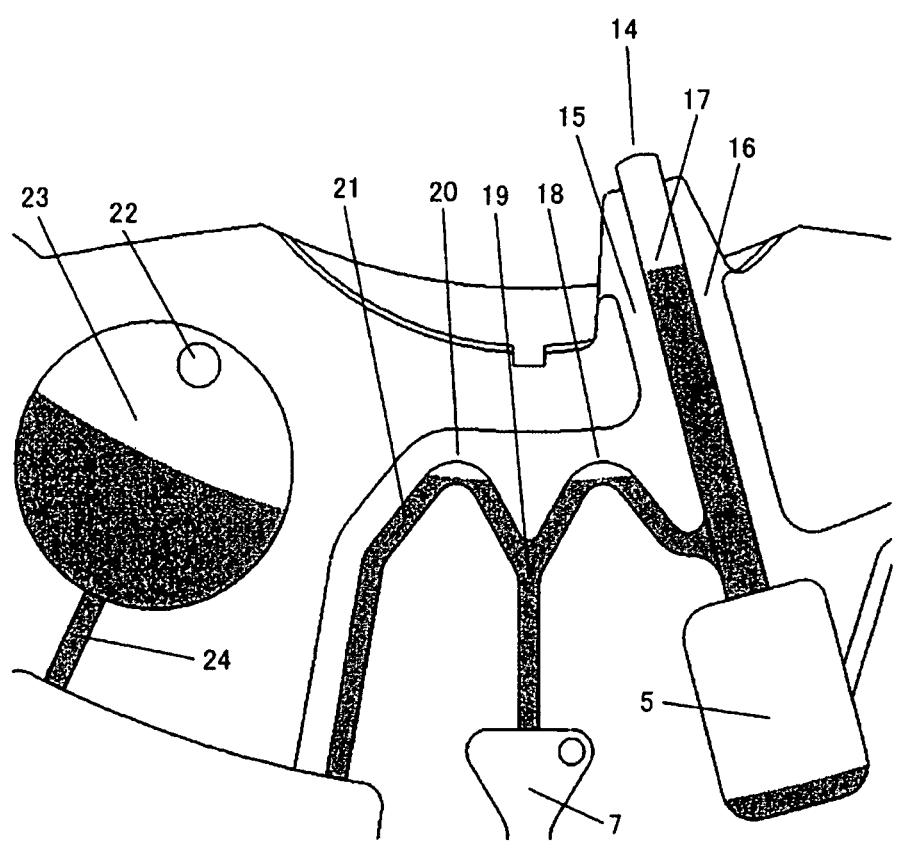
FIG. 11 is an enlarged view illustrating a "liquid sample distribution process" of Embodiment 2.
Figure 12:
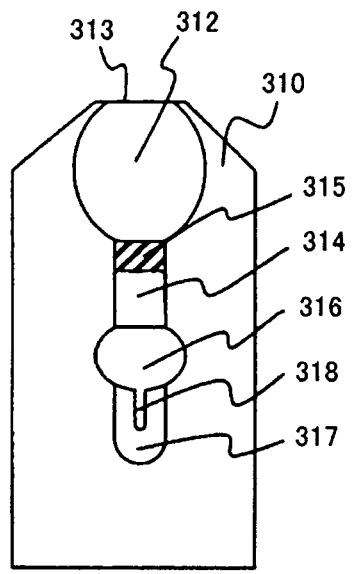
FIG. 12 is a diagram showing the structure of a conventional centrifugal transfer biosensor.

FIG. 9 through FIG. 11 show Embodiment 2 of the present invention.

FIG. 9 is a plan view of the microchannel structure of a microchip of Embodiment 2. FIG. 10 is a diagram illustrating a "microchip liquid sample introduction process" through to a "measuring chamber filling process", of Embodiment 2. FIG. 11 is an enlarged view illustrating a "microchip liquid sample distribution process" of Embodiment 2 of the present invention.

Note that the main structure of the microchip of Embodiment 2 and the structure of an analyzer 1000 on which the microchip of Embodiment 2 is mounted are the same as those described in Embodiment 1, and therefore will not be described here.

As shown in FIG. 9, the microchannel structure of a microchip 3 of Embodiment 2 includes: an inlet 14 for collecting a liquid sample therethrough; a first capillary cavity 17 for holding a predetermined amount of the liquid sample introduced into the inlet 14; a second capillary cavity 19 for holding a predetermined amount of the liquid sample through the first capillary cavity 17; a third capillary cavity 21 for holding a predetermined amount of the liquid sample through the second capillary cavity 19; cavities 15 and 16 for expelling the air from the capillary cavities 17 and 19; a holding chamber 5, acting as a storage chamber or a first holding chamber, for receiving the liquid sample from the first capillary cavity 17 and separating the liquid sample including a solid component, into a solution component and the solid component; a measuring chamber 7 acting as a second holding chamber for receiving the liquid sample from the second capillary cavity 19 and measuring the ratio of the solution component to the solid component in the liquid sample; a measuring chamber 25 acting as a third holding chamber for receiving the liquid sample from the third capillary cavity 21 and a dilute solution introduced into a dilute solution storage chamber 23, mixing the received liquid sample and dilute solution therein, and measuring the components in the liquid sample; a fourth capillary cavity 28 for holding, through a channel 26, a predetermined amount of the solution component of the liquid sample that is separated in the holding chamber 5; a fifth capillary cavity 30 for holding a predetermined amount of the solution component through the fourth capillary cavity 28; a measuring chamber 34 acting as a fourth holding chamber for receiving the liquid sample from the fourth capillary cavity 28 and measuring the mixture of the liquid sample and an analytical reagent; a measuring chamber 38 acting as a fifth holding chamber for receiving the liquid sample from the fifth capillary cavity 30 and measuring the mixture of the liquid sample and an analytical reagent; a channel 33 for communicating with the measuring chamber 34 and a valve 31 communicating with the end of the fourth capillary cavity 28; a channel 35 for connecting the measuring chamber 34 with an atmospheric vent 36; a channel 37 for communicating with the measuring chamber 38 and a valve 32 communicating with the end of the fifth capillary cavity 30; and a channel 39 for connecting the measuring chamber 38 with an atmospheric vent 40.

Here in the present invention, the first capillary cavity 17, the second capillary cavity 19, the third capillary cavity 21, a channel 24, the channel 26, the fourth capillary cavity 28, the fifth capillary cavity 30, the channel 33, the channel 35, the channel 37, and the channel 39 are each formed with depths of 50 μm to 300 μm, but may not be limited to these sizes so long as the liquid sample can flow through each element by capillary force. Further, the holding chamber 5, the measuring chamber 7, the dilute solution storage chamber 23, the cavities 15 and 16, the measuring chamber 25, the valves 31 and 32, the measuring chamber 34, and the measuring chamber 38 are each formed with depths of 0.3 mm to 5 mm, but these depths can be adjusted in accordance with the amount of a sample solution and the conditions of absorbance measurement (an optical path length, a measurement wavelength, the reaction concentration of the sample solution, the type of a reagent, etc.).

In Embodiment 2, the walls of the first capillary cavity 17, the second capillary cavity 19, the third capillary cavity 21, the channel 24, the channel 26, the fourth capillary cavity 28, the fifth capillary cavity 30, the channel 33, the channel 35, the channel 37, and the channel 39 are subjected to a hydrophilic treatment so that the liquid sample can flow through each element by capillary force. The hydrophilic treatment method may include a surface treatment method that uses active gas such as plasma, corona, ozone, and fluorine, and may also include a surface treatment by a surface active agent and a hydrophilic polymer. Here, hydrophilicity is obtained when the contact angle with water is less than 90°, and more preferably, less than 40°.

Next, with reference to FIG. 10, the transfer process of a liquid sample will be described in detail.

First, in order to supply the liquid sample to the microchip 3 having this structure, the liquid sample is applied as a droplet to the inlet 14, which protrudes from one side surface of the microchip 3 toward an axis 11, when the microchip 3 is detached from a microchip holding member 101. Immediately after the droplet is applied, a predetermined amount of the liquid sample is introduced into the first capillary cavity 17 by capillary action, a predetermined amount of the liquid sample is then introduced into the second capillary cavity 19 through the first capillary cavity 17, and a predetermined amount of the liquid sample is then introduced into the third capillary cavity 21 through the second capillary cavity 19, as shown in FIG. 10A.

At this time, in the present invention, the cavities 15 and 16 are provided to opposite sides of the first capillary cavity 17 and sides of the second capillary cavity 19 and the third capillary cavity 21 on the inner peripheral side, so as to expel the air from the respective capillary cavities. Thus, the capillary flow of the liquid sample filling each capillary cavity flows ahead not in the side portion of the capillary cavity, but in the center portion of the capillary cavity.

Consequently, even when the liquid sample to be applied as a droplet to the inlet 14 runs short while filling each capillary cavity, or even when the liquid sample is separated from the inlet 14 while filling each capillary cavity, another droplet may be reapplied to the inlet, so that the reapplied liquid sample flows ahead in the center portion of each capillary cavity, and therefore contacts the center portion of the liquid sample held in the capillary cavity and fills the capillary cavity while expelling the air in the direction of the side or in the directions of the sides on which either or both of the cavities 15 and 16 are provided. As a result, air bubbles are not produced, and droplets can be applied any number of times until each capillary cavity can hold a predetermined amount of the liquid sample.

The arrangements of the first capillary cavity 17, the second capillary cavity 19, the third capillary cavity 21, and the cavities 15 and 16 are similar to the corresponding arrangements described in Embodiment 1, and therefore will not be described.

After the first capillary cavity 17, the second capillary cavity 19, and the third capillary cavity 21 are filled with the liquid sample, a predetermined amount of dilute solution is introduced into the dilute solution storage chamber 23 through an inlet 22. Then, the microchip 3 is mounted on the analyzer 1000 and is rotated by the rotary drive means of the analyzer 1000, whereby, as shown in FIG. 10B, the liquid sample in the first capillary cavity 17, which has been held between the inlet 14 and a first distribution point 18 acting as a boundary, parts at the first distribution point 18 and is transferred to the holding chamber 5 by centrifugal force. Further, the liquid sample in the second capillary cavity 19, which has been held between the first distribution point 18 and a second distribution point 20 acting as a boundary, parts at the first distribution point 18 and the second distribution point 20 and is transferred to the measuring chamber 7 by centrifugal force. Furthermore, the liquid sample in the third capillary cavity 21, which has been held between the second distribution point 20 and the measuring chamber 25, parts at the second distribution point 20 and is transferred to the measuring chamber 25 by centrifugal force. Additionally, the dilute solution in the dilute solution storage chamber 23 is transferred to the measuring chamber 25 through the channel 24 by centrifugal force.

Figure 14A:
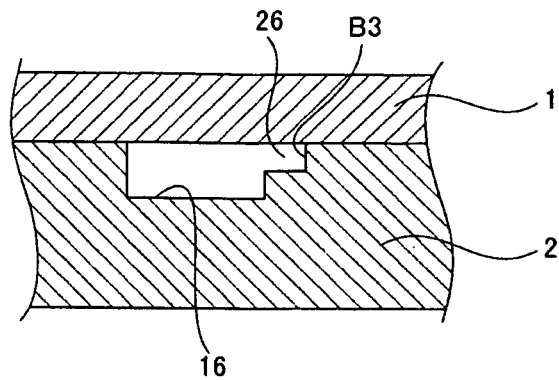
FIG. 14A to FIG. 14C are cross-sectional views taken along line A-A', line C-C', and line D-D' of FIG. 9, respectively.
Figure 14B:
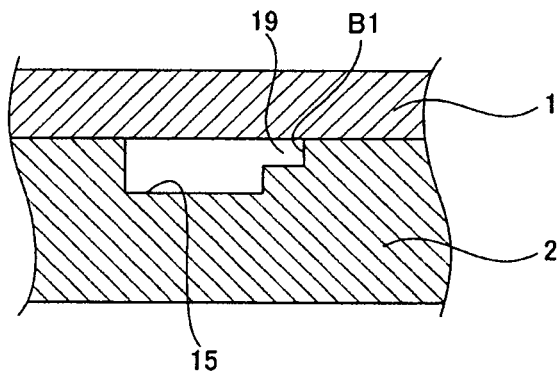
Figure 14C:
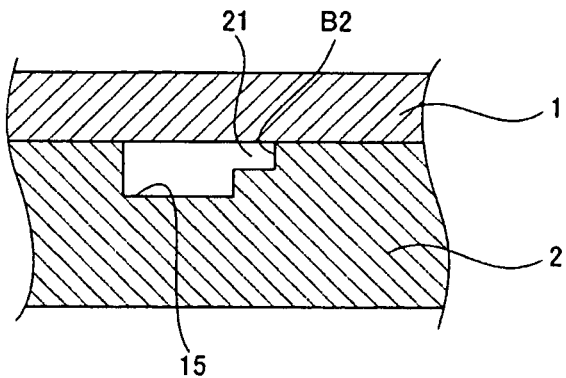

Here in the present invention, the first distribution point 18, which is the boundary between the first capillary cavity 17 and the second capillary cavity 19, and the second distribution point 20, which is the boundary between the second capillary cavity 19 and the third capillary cavity 21, each have a curved shape, projecting in the inner peripheral direction, on the inner peripheral side with respect to the holding chamber 5, the measuring chamber 7, and the measuring chamber 25. Further, the cavities 15 and 16 are provided to the sides of the first capillary cavity 17, the second capillary cavity 19, and the third capillary cavity 21. Thus, when the liquid sample in each capillary cavity is transferred in the outer peripheral direction by centrifugal force, a pressure difference between the capillary cavities and a siphon effect are less likely to occur, even if centrifugal force acts on the liquid sample from the radially innermost positions of the first distribution point 18 and the second distribution point 20 and thus parts the liquid sample, as shown in FIG. 11. This makes it possible to distribute the liquid sample to each capillary cavity with high accuracy. FIGS. 14A, 14B and 14C show cross-sectional views taken along line A-A', line C-C', and line D-D' of FIG. 9, respectively. The first distribution point 18, which is the boundary between the first capillary cavity 17 and the second capillary cavity 19, has a curved shape, projecting in the inner peripheral direction, on the inner peripheral side with respect to the holding chamber 5 and the measuring chamber 7 acting as the second holding chamber, and has a wall B1 on the outer peripheral side.

Further, the second distribution point 20, which is the boundary between the measuring chamber 7 acting as a holding chamber and the third capillary cavity 21 formed contiguously thereto, has a curved shape, projecting in the inner peripheral direction, on the inner peripheral side with respect to the holding chamber 5 and the measuring chamber 7 acting as the second holding chamber, and has a wall B2 on the outer peripheral side.

Furthermore, a third distribution point 27, which is the boundary between the fourth capillary cavity 28 and the fifth capillary cavity 30, has a curved shape, projecting in the inner peripheral direction, on the inner peripheral side with respect to the holding chamber 5 and the second holding chamber, and has a wall B3 on the outer peripheral side.

Figure 13:
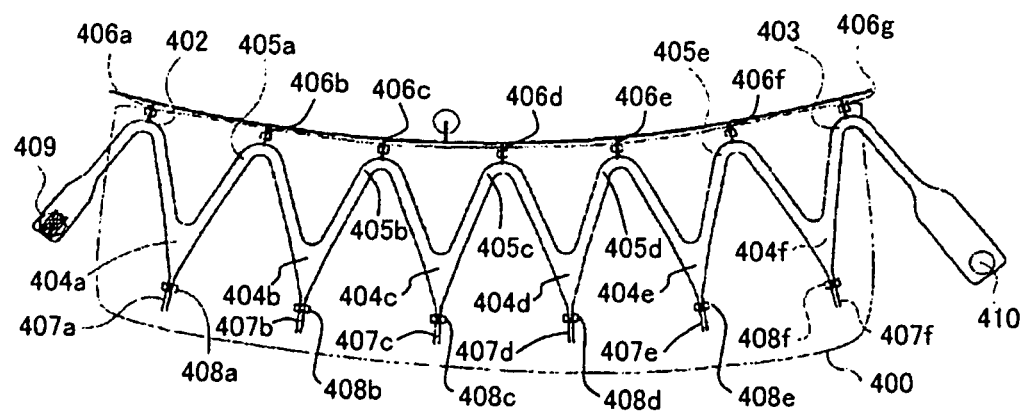
FIG. 13 is a diagram illustrating liquid sample distributions of a conventional centrifugal transfer biosensor.

Conventionally, with the structure as shown in FIG. 13 where air vents are provided only at the distribution points of capillary cavities, when a liquid sample having filled a capillary cavity is distributed and transferred by centrifugal force, a pressure difference or a siphon effect may occur in some capillary cavities, when centrifugal force is applied, due to differences in the amount of liquid or between the cross-sectional sizes of the capillary cavities. Therefore, a larger amount of the liquid sample than a predetermined amount may be drawn and flow into either one of the capillary cavities until the liquid sample parts at the distribution point therebetween. This makes it impossible to distribute and transfer the liquid sample with high accuracy.

The structure of the present embodiment, however, makes it possible to distribute the liquid sample from a capillary cavity without causing a pressure difference between capillary cavities or a siphon effect, and therefore improve the distribution accuracy of the liquid sample.

Further, the number of distributions of the liquid sample can be adjusted in accordance with the number of measurement items. When N distributions are required, N capillary cavities can be provided so that each capillary cavity communicates with holding chambers such as a mixing chamber and a measuring chamber. Thus, the number of distributions may not be limited to the descriptions of Embodiment 2.

Further, in the present invention, the capillary cavities to be filled with the liquid sample are formed contiguously, in one direction, from one point of the first capillary cavity 17 communicating with the inlet 14, but the liquid sample may fill capillary cavities formed contiguously, in both left and right directions, from two or more points of the first capillary cavity 17.

The liquid sample having flowed into the holding chamber 5 and the measuring chamber 7 is separated into a solution component and a solid component by centrifugal force. Additionally, the liquid sample and the dilute solution having flowed into the measuring chamber 25 are mixed with each other by vibrations due to the acceleration of the rotation of the analyzer 1000 or by the diffusion of the liquid while the rotation is stopped, but can also be mixed under the action of an external force that directly vibrates the measuring chamber 25 per se.

Next, when the separation of the liquid sample in the holding chamber 5 reaches a predetermined level, the rotation of the microchip 3 stops. Then, as shown in FIG. 10C, only a predetermined amount of the solution component in the holding chamber 5 fills the fourth capillary cavity 28 through the channel 26 by capillary force, and further, only a predetermined amount of the solution component fills the fifth capillary cavity 30 through the fourth capillary cavity 28 by capillary force.

At the end of the fourth capillary cavity 28, the valve 31 having a greater section size in the thickness direction than that of the fourth capillary cavity 28 is provided so that the capillary flow of the liquid sample having flowed into the fourth capillary cavity 28 stops at the valve 31. Similarly, at the end of the fifth capillary cavity 30, a valve 32 having a greater section size in the thickness direction than that of the fifth capillary cavity 30 is provided so that the capillary flow of the liquid sample having flowed into the fifth capillary cavity 30 stops at the valve 32.

At this time, in the present invention, the cavity 16 is provided to the sides of the fourth capillary cavity 28 and the fifth capillary cavity 30, on the inner peripheral side, so as to expel the air from each capillary cavity. Thus, the capillary flow of the liquid sample filling each capillary cavity flows ahead in the side portion of the capillary cavity, on the outer peripheral side. Consequently, the liquid sample from the holding chamber 5 fills each capillary cavity while expelling the air in the direction of the side, on the inner peripheral side, to which the cavity 16 is provided. As a result, air bubbles are not produced in the capillary cavities, and each capillary cavity can be filled with the liquid sample.

The arrangements of the fourth capillary cavity 28, the fifth capillary cavity 30, the channel 26, and the cavity 16 are similar to the corresponding arrangements described in Embodiment 1, and therefore will not be described.

After the fourth capillary cavity 28 and the fifth capillary cavity 30 are filled, the microchip 3 is rotated by the rotary drive means of the analyzer 1000, whereby, as shown in FIG. 10D, the liquid sample in the fourth capillary cavity 28, which has been held between the third distribution point 27 and a fourth distribution point 29 acting as a boundary, parts at the third distribution point 27 and the fourth distribution point 29 and is transferred to the measuring chamber 34 through the valve 31 and the channel 33 by centrifugal force. Further, the liquid sample in the fifth capillary cavity 30, which has been held between the fourth distribution point 29 and the valve 32, parts at the fourth distribution point 29 and is transferred to the measuring chamber 38 through the valve 32 and the channel 37 by centrifugal force.

Here in the present invention, the third distribution point 27, which is the boundary between the channel 26 and the fourth capillary cavity 28, and the fourth distribution point 29, which is the boundary between the fourth capillary cavity 28 and the fifth capillary cavity 30, each have a curved shape, projecting in the inner peripheral direction, on the inner peripheral side with respect to the measuring chamber 34 and the measuring chamber 38. Further, the cavity 16 is provided to the sides of the fourth capillary cavity 28 and the fifth capillary cavity 30. Thus, when the liquid sample in each capillary cavity is transferred in the outer peripheral direction by centrifugal force, a pressure difference between the capillary cavities and a siphon effect are less likely to occur, even if centrifugal force acts on the liquid sample from the radially innermost positions of the third distribution point 27 and the fourth distribution point 29 and thus parts the liquid sample. This makes it possible to distribute the liquid sample to each capillary cavity with high accuracy.

Further, the number of distributions of the liquid sample can be adjusted in accordance with the number of measurement items. When N distributions are required, N capillary cavities can be provided so that each capillary cavity communicates with holding chambers such as a mixing chamber and a measuring chamber. Thus, the number of distributions may not be limited to the descriptions of Embodiment 2.

Further, in the present invention, the capillary cavities to be filled with the liquid sample are formed contiguously, in one direction, from one point of the holding chamber 5, but the liquid sample may fill capillary cavities formed contiguously, in both left and right directions, from two or more points of the holding chamber 5.

A measuring device (not shown) mounted on the analyzer can measure the reaction state of the liquid sample and the analytical reagent by absorbance measurement and the like, whereby it is possible to measure the concentration of a component of the liquid sample transferred to the measuring chamber 34 and the measuring chamber 38.

When the liquid sample is blood, it is possible to measure hematocrit (the ratio of blood cells to blood plasma) in the measuring chamber 7, measure hemoglobin concentration of erythrocytes in the measuring chamber 25, and measure the glucose content in blood plasma and a lipid component such as cholesterol, using the blood plasma separated in the holding chamber 5.

INDUSTRIAL APPLICABILITY

A microchip according to the present invention is capable of preventing air bubbles from forming in a capillary cavity for collecting a liquid sample and thus capable of collecting the liquid sample any number of times until the capillary cavity is full, and also is capable of improving the distribution accuracy of the liquid sample, and therefore the microchip is useful for a liquid sample collection method, a liquid sample distribution transfer method, and the like in a microchip used for component measurement of a biological fluid performed by an electrochemical sensor or an optical sensor.

The invention claimed is:

1. A microchip, having therein:
   an inlet (14) that collects a liquid sample therethrough, the inlet (14) protruding from one side surface of the microchip;
   a capillary cavity (4) configured such that an upper face and a lower face in a thickness direction are opposed to a gap generating a capillary force, the capillary cavity (4) sucking the liquid sample from the inlet (14) located at a first end of the capillary cavity (4) to a second end of the capillary cavity (4) by the capillary force and retaining therein and having an opening from the first end to the second end in one side face of the capillary cavity (4); and
   a holding chamber (5) provided at the second end of the capillary cavity (4),
   wherein the microchip transfers the liquid sample retained in the capillary cavity (4) to the holding chamber (5) by a centrifugal force generated by a rotation about an axis of rotation and analyzes therein, a side cavity (15,16) is provided at a side along a flow direction of the liquid sample in the capillary cavity (4), the side cavity (15,16) being configured such that an upper face and a lower face in a thickness direction are opposed to a gap not generating a capillary force but being always in communication with an atmosphere, the opening provided in the one side face of the capillary cavity (4) is always opened to an inside of the side cavity (15,16) from the first end to the second end of the capillary cavity (4), when the liquid sample is sucked into the capillary cavity (4), air in the capillary cavity (4) is expelled to the side cavity (15, 16) by the liquid sample sucked into the capillary cavity (4) and moves from the first end of the capillary cavity (4) to the second end of the capillary cavity (4).

2. The microchip according to claim 1, wherein cross-sectional shapes of the capillary cavity and the side cavity are rectangular; the side cavity is greater in cross-sectional thickness than the capillary cavity; and the side cavity is adjacent to one side or opposite sides of the capillary cavity.

3. The microchip according to claim 1, wherein a portion of a cross section of the capillary cavity is arc-shaped;
   a cross section of the side cavity is rectangular;
   the side cavity is greater in cross-sectional thickness than the capillary cavity; and
   the side cavity is adjacent to one side or opposite sides of the capillary cavity.

4. The microchip according to claim 2, wherein
   the side cavity is at least 50 μm greater in cross-sectional thickness than the capillary cavity.

5. The microchip according to claim 1, wherein portions of cross sections of the capillary cavity and the side cavity are arc-shaped; and the side cavity is adjacent to one side or opposite sides of the capillary cavity.

6. The microchip according to claim 1, wherein a wall of the side cavity is a hydrophobic surface.

7. A microchip, having therein:
   a holding chamber (5) that holds a liquid sample;
   a channel (26) configured such that an upper face and a lower face in the thickness direction are opposed to a gap generating a capillary force, the channel (26) sucking a liquid sample from the holding chamber (5) through a first end of the channel (26) to a second end of the channel (26) by the capillary force and retaining therein and having an opening from the first end to the second end in one side face of the channel (26); and
   a measuring chamber (34, 38) connected to the second end of the channel (26);
   wherein the microchip transfers the liquid sample retained in the channel (26) to the measuring chamber (34, 38) by a centrifugal force generated by a rotation about an axis of rotation and analyzes therein, a side cavity (16) is provided at a side which is along a flow direction of the liquid sample in the channel (26) and closer to the axis of rotation, the side cavity (16) being configured such that an upper face and a lower face in a thickness direction are opposed to a gap not generating a capillary force but being always in communication with an atmosphere, whole area of the side which is along a flow direction of the liquid sample in the channel (26) and closer to the axis of rotation is always opened to an inside of the side cavity (16), when the liquid sample is sucked into the channel (26), air in the channel (26) is expelled to the side cavity (16) by the liquid sample sucked into the channel (26) and moves from the first end of the channel (26) to the second end of the channel (26).

* * * * *